(12) United States Patent
Brown

(10) Patent No.: US 9,445,892 B2
(45) Date of Patent: *Sep. 20, 2016

(54) INTRACAPSULAR PSEUDOPHAKIC DEVICE

(76) Inventor: David C. Brown, Fort Myers, FL (US)

( * ) Notice: Subject to any disclaimer, the term of this patent is extended or adjusted under 35 U.S.C. 154(b) by 1107 days.

This patent is subject to a terminal disclaimer.

(21) Appl. No.: 12/854,645

(22) Filed: Aug. 11, 2010

(65) Prior Publication Data

US 2010/0324674 A1  Dec. 23, 2010

Related U.S. Application Data

(62) Division of application No. 10/927,743, filed on Aug. 27, 2004, now Pat. No. 7,806,929.

(51) Int. Cl.
*A61F 2/14* (2006.01)
*A61F 2/16* (2006.01)

(52) U.S. Cl.
CPC ........... *A61F 2/1602* (2013.01); *A61F 2/1648* (2013.01); *A61F 2/1624* (2013.01); *A61F 2/1694* (2013.01)

(58) Field of Classification Search
CPC .. A61F 2/1602; A61F 2/1648; A61F 2/1651; A61F 2/14; A61F 2220/0008; A61F 2250/006–2250/0063; A61F 2250/0065; A61F 2250/0069; A61F 2250/0091; A61F 2250/007
USPC .......... 623/5.12–5.14, 6.15–6.16, 6.32–6.34, 623/6.37–6.55
See application file for complete search history.

(56) References Cited

U.S. PATENT DOCUMENTS

| 4,253,199 | A | * | 3/1981 | Banko | 623/6.13 |
| 4,585,457 | A | * | 4/1986 | Kalb | 623/6.13 |
| 4,902,293 | A | * | 2/1990 | Feaster | 623/6.13 |
| 4,932,966 | A | * | 6/1990 | Christie et al. | 623/6.13 |
| 5,171,320 | A | * | 12/1992 | Nishi | 623/6.39 |
| 5,275,623 | A | * | 1/1994 | Sarfarazi | 623/6.13 |
| 6,027,531 | A | * | 2/2000 | Tassignon | 623/6.4 |
| 6,068,643 | A | * | 5/2000 | Milverton | 606/191 |
| 6,258,123 | B1 | * | 7/2001 | Young et al. | 623/6.16 |
| 6,551,354 | B1 | * | 4/2003 | Ghazizadeh et al. | 623/6.43 |
| 6,616,692 | B1 | * | 9/2003 | Glick et al. | 623/6.34 |
| 6,645,246 | B1 | | 11/2003 | Weinschenk et al. | |
| 7,597,678 | B2 | * | 10/2009 | Brown | 604/8 |
| 7,806,929 | B2 | | 10/2010 | Brown | |
| 2002/0107568 | A1 | | 8/2002 | Zadno-Azizi et al. | |
| 2003/0060878 | A1 | * | 3/2003 | Shadduck | 623/6.13 |
| 2004/0010284 | A1 | * | 1/2004 | Maloof et al. | 606/213 |
| 2004/0082993 | A1 | * | 4/2004 | Woods | 623/6.28 |

FOREIGN PATENT DOCUMENTS

WO    WO 03/022191 A1 *  3/2003 ............. A61F 9/007

* cited by examiner

*Primary Examiner* — Paul Prebilic
(74) *Attorney, Agent, or Firm* — Tumey L.L.P.

(57) ABSTRACT

Intraocular devices for use in and attached to the natural lens capsule of an eye are provided. The lens capsule may be maintained in a configuration to avoid post-operative changes that are deleterious to vision. Single or dual optic systems are provided, which may be accommodating. Combinations of devices to obtain dual optic systems are disclosed.

3 Claims, 10 Drawing Sheets

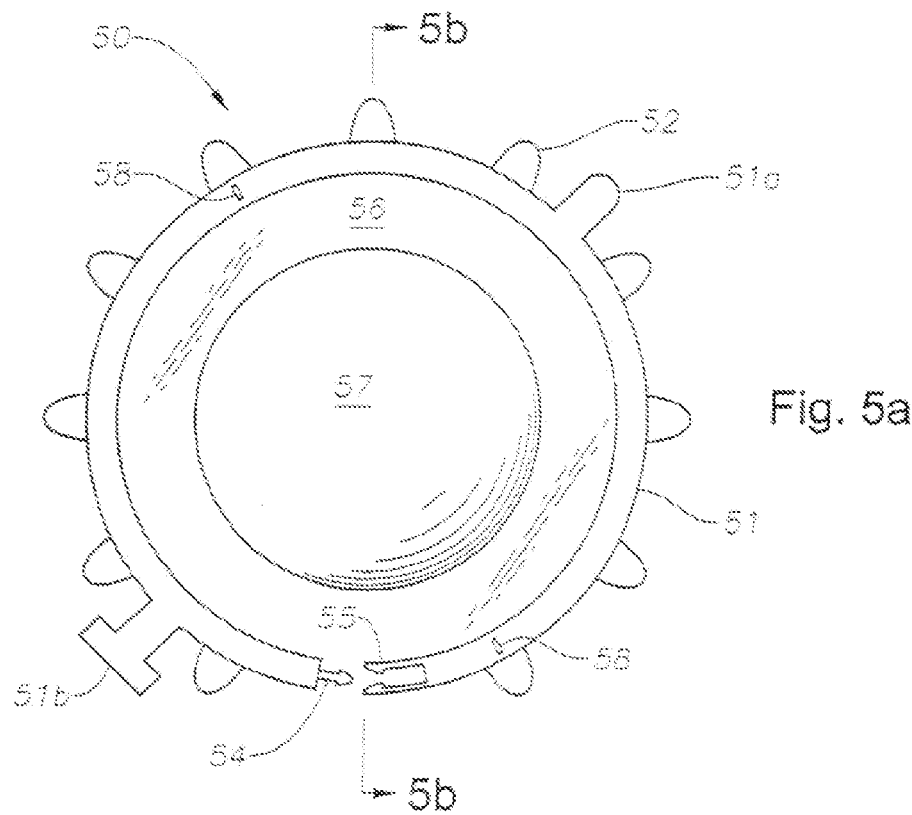
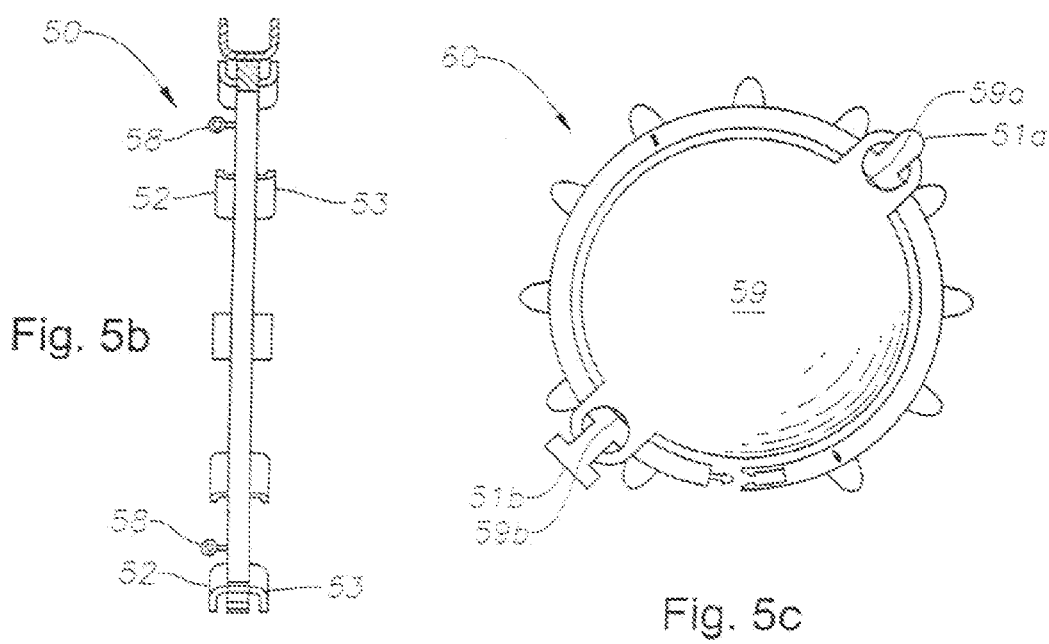
Fig. 5a
Fig. 5b
Fig. 5c

INTRACAPSULAR PSEUDOPHAKIC DEVICE

This is a divisional application of U.S. patent application Ser. No. 10/927,743 filed on Aug. 27, 2004.

BACKGROUND OF THE INVENTION

1. Field of the Invention

This invention pertains to apparatus and method for supplying an intra-ocular lens (IOL) to an eye, which may be an accommodating lens, and providing other benefits in treatment of the natural lens of an eye. More particularly, a structure adapted to be placed in a human lens capsule along with one or two lens optics is supplied, along with methods of using.

2. Description of Related Art

A young human eye has a natural "accommodation" ability, which is the ability to focus on both near and far objects. Contraction and relaxation of the ciliary muscle provides the eye with this ability. Ciliary muscle action shapes the natural crystalline lens in the eye to the appropriate optical configuration for focusing light rays entering the eye on the retina. Because of physiological changes with age, the human eye often loses this natural accommodation ability and develops a condition called "presbyopia." Furthermore, the natural crystalline lens often develops a cataract, which is an opaque region of the lens. This condition leads to widespread application of techniques to remove the natural crystalline lens. Often a conventional intra-ocular lens (IOL) is then placed in the eye. The conventional (monofocal) IOL has very limited, if any, accommodating ability. The wearer or user of the conventional IOL then may use corrective spectacles as a useful aid in vision. Multifocal IOL's without accommodating movement have been used to provide near and far vision correction.

A variety of attempts have been made to provide IOL's with accommodating movement in the eye. One such device is the CRYSTALENS, which was approved for use in the United States in November, 2003. (Another accommodating lens has been approved for use in Europe.) The CRYSTALENS has a single optic attached to hinged haptics. The optic is vaulted in the posterior position against the posterior capsule. Operation of the ciliary muscle increases the pressure in the vitreous humor, moving the optic in an anterior direction, thereby increasing the power of the optic. Relaxation of the ciliary muscle allows the lens to move backward. The forward and backward motion simulates natural lens accommodation. The amount of accommodation is limited, however. The CRYSTALENS normally includes a relatively small optic zone to enhance optic movement, but thereby this increases the chances of nighttime glare and halos.

Another approach to obtaining accommodation is disclosed in U.S. Pat. No. 6,645,246 B1. An accommodating IOL employs an optic made of two different materials to enhance the accommodation achievable in the eye in response to normal accommodative stimuli. The optic includes a first lens portion surrounding a second lens portion that is less deformable than the first portion. The optic can be sized and configured to fit within the capsular bag.

Researchers have envisioned a soft, elastic polymer gel that may someday be used to replace the clouded natural lens that is removed during cataract surgery. This approach is considered by some researchers also as a possible mechanism to correct presbyopia. The gel would be injected into the capsular bag after the eye's natural lens is removed. The material may be a modified hydrogel, similar to that used for extended wear contact lenses. Its injectability could eliminate the need for the larger incision that is normally required to insert a replacement IOL. One of the limitations of this approach is that the gel must have a high refractive index. Also, a method for re-sealing the lens capsule will be required.

When IOLs are placed in the capsule of an eye, tissue growth around the haptics or other position fixation apparatus occurs, particularly when the lens has been implanted for an extended period of time. Also, adhesion of tissue to the lens or its haptics occurs. This, in most cases, eliminates the possibility of removing or adjusting an existing implanted lens and replacing it with a more efficacious optic. Also, when greater accommodation is needed using accommodating IOLs, keeping the lens capsule open would be beneficial. Pressure change in the vitreous humor because of muscle contraction will have greater effect on movement of an accommodating lens apparatus if volume of the capsule is maintained at a higher value. Holding the lens capsule open will also prevent the fusion of the anterior and posterior capsules and allow greater ease of accommodation and flexibility of the complex. Apparatus and method that would allow these further procedures in a pseudophakic eye are needed.

Surgical procedures to form an opening (capsulorhexis) in both the anterior capsule and the posterior capsule are sometimes necessary. Particularly in the eyes of younger patients, the capsule opening is closed by growth of tissue in a relatively short time. Particularly in pediatric ophthalmology, there is a need for surgical apparatus and method to avoid the rapid closure of such openings. In adults, pseudoexfoliation syndrome is also complicated by contraction of the capsule (phimosis) with resultant visual disturbance and damage to supporting zonules.

Contraction of the anterior capsule also occurs in eyes where the CRYSTALENS has been implanted. The capsular contraction can cause posterior displacement of the CRYSTALENS, resulting in hyperopia, or extreme contraction of the capsule results in asymmetric compression of the CRYSTALENS with significant power changes including myopia and astigmatism, e.g., "Z Compression."

What is needed is apparatus and method for providing accommodating lenses that allow greater range of accommodation, allowing a user to obtain near and distant vision without eyeglasses. When openings are surgically formed in the capsule to implant IOLs or perform other surgical procedures, there is a need to provide apparatus and procedure to maintain the form of the lens capsule and to maintain the diameter of a capsulotomy opening.

SUMMARY OF INVENTION

In one embodiment of the present invention, a lens optic having haptics attached is implanted within the capsular bag. The haptics extend from the lens, placed in contact with the posterior capsule, so as to maintain the volume of the lens capsule and prevent fibrosis or collapse and fusion of the anterior and posterior capsule. The haptics may have a spiral structure or other forms, which are radially displaced around the optic and have dimension's allowing the haptic to extend around the interior of the capsule past the fornix. The optic may be a light-adjustable lens. In another embodiment, a capsulotomy ring is placed and fitted within the capsulorhexis, and the ring may include haptics that extend posteriorly toward the posterior capsule. The ring may also include a membrane or an optic. The optic may be attached to the ring after the ring is implanted. In another embodiment, an artificial capsule is implanted within the natural lens capsule. The artificial capsule may contain liquid, gel or other deformable medium, such that it is deformed in response to the action of ciliary muscle, changing the power of the lens. An external conduit that is removable and reattachable to a valve in the implantable capsule may be used for adjusting the volume of the capsule. In other embodiments, an artificial anterior capsule is provided. The artificial anterior capsule, including a membrane, may be used to prevent extrusion of the artificial capsule from the natural capsule. Further, the artificial anterior capsule may include an optic. The membrane may be deformable, so as to respond to pressure changes in the capsule and provide an accommodating lens system. The optic may be a light-adjustable lens. The artificial anterior capsule may be provided by a membrane affixed around the periphery of an opening in the natural anterior capsule by a collar or a pinched segment of the natural anterior capsule. Combinations of the disclosed devices may provide dual optic devices.

BRIEF DESCRIPTION OF THE DRAWINGS

The same numerals in different drawings indicate the same parts of an eye and the same parts of a disclosed apparatus.

FIGS. 5a and 5b show a plan view and side view of an alternate embodiment of an intracapsulotomy ring to be placed in the capsule opening. FIG. 5c shows a plan view of the ring of FIG. 5a with an optic attached to the top of the ring.

DETAILED DESCRIPTION

Figure 1:
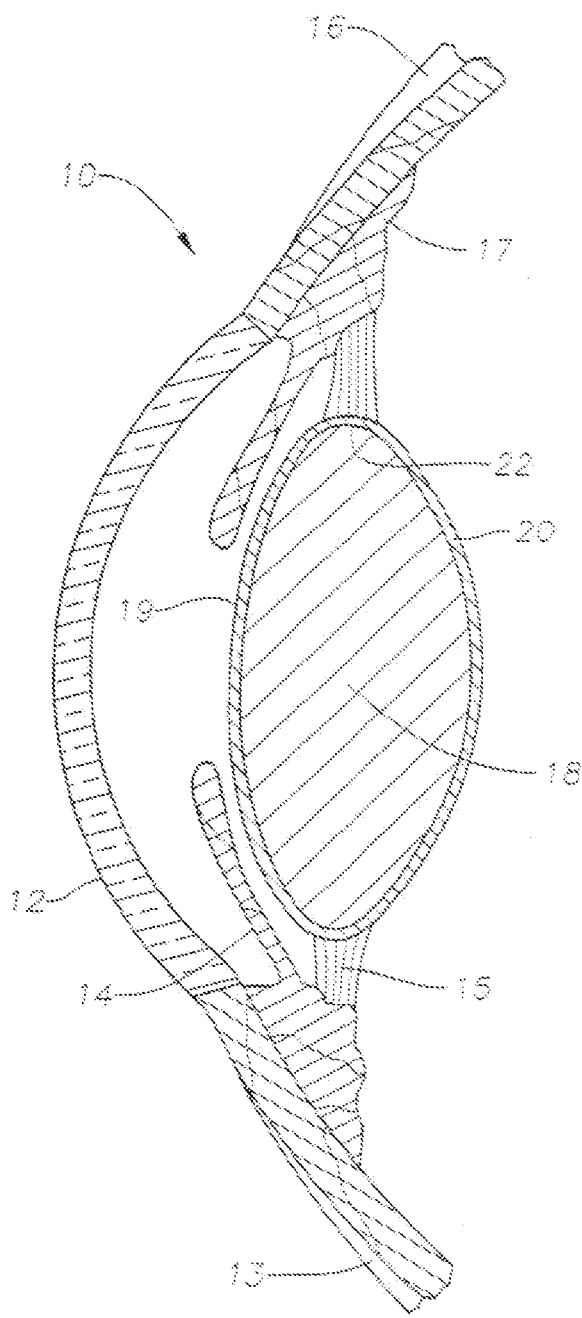
FIG. 1 shows a cross-sectional view of the anterior portion of a human eye.

Referring to FIG. 1, a cross-sectional view of the anterior portion on an eye, which may be a human eye, is shown. Eye 10 includes cornea 12, sclera 13, iris 14, zonules 15, conjunctiva 16, ciliary body 17, lens capsule 18, anterior capsule 19, posterior capsule 20 and capsule equator or fornix 22. The development of presbyopia and cataracts in the human eye are associated with changes in natural lens capsule 18 and its contents. Surgical procedures to remove cataracts from lens capsule 18 or to implant intraocular lenses, either accommodating or fixed, involve making an incision through cornea 12 or sclera 13 and forming an opening in capsule 19 (a capsulorhexis). The size of the external incision is minimized to limit trauma to the patient's eye and allow faster healing. Common sizes of the incision are 2.5 to 3 millimeters, however there is a trend to make smaller incisions, such as 1.5 millimeter.

Figure 2A:
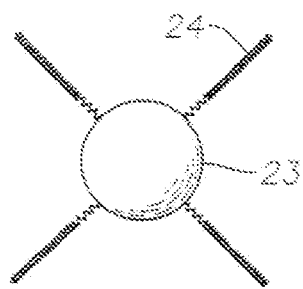
FIG. 2a shows a plan view and FIG. 2b a side view of an optic having haptics formed from coiled members.
Figure 2B:
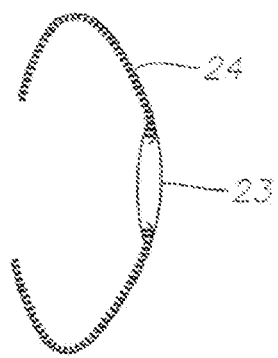
FIG. 2c shows a plan view of an optic having haptics that form a spiral.
FIG. 2d shows a plan view of an optic having haptics formed from strips having flexible hinges.
FIG. 2e is a plan view and FIG. 2f is a side view of an optic having haptics formed from continuous loops.
FIG. 2g is a plan view and FIG. 2h is a side view of an optic having haptics formed from plates having distal support members.
Figure 2C:
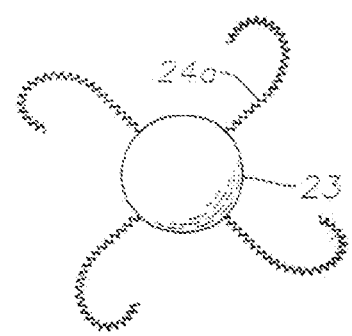

FIG. 2a shows a plan view of an optic and attached haptics according to one embodiment of the present disclosure. Optic 23 may be a rigid lens or may be adaptable to folding for insertion in the eye through a smaller incision. Such foldable lenses are widely used in the art. Optic 23 may be a light-adjustable lens, such as is available from Calhoun Vision, Inc., Pasadena, Calif., disclosed in U.S. Patent Application Publication No. 2003/0174375, published Sep. 18, 2003, which is incorporated by reference herein. In one embodiment, haptics 24 are in a spiral configuration of a deformable material suitable for biomedical use, such as materials disclosed in U.S. Patent Application 2002/0175846, for example, which is incorporated by reference herein. Such materials for lenses and haptics are well known in the art and may be selected based on available material modulus and other physical properties. Haptics 24 may be integrally formed with lens 23 or may be attached by various known mechanical attachment methods. The spiral configuration may be formed from strands of polymeric material. Alternatively, the strands may be used to form haptics without formation of the spiral configuration. FIG. 2b shows a side view of the device of FIG. 2a. Haptics may be linearly extended in the absence of a force on the haptic, or haptics 24 may be formed to a preset position, such as conforming to the interior of a natural lens capsule in the absence of a bending force on the haptic, before insertion in an eye. Haptics may also be curved in a plane parallel to the lens plane, such as shown in FIG. 2c, where haptics 24a attached to lens 23 are illustrated. Preferably, haptics 24 or 24a are deformable and foldable such that they may be folded into a position near lens 23 while the device is placed in an eye. The modulus of the material used to form a spiral haptic or the cross-sectional area of the material along the length of the haptic may be varied in a selected manner so as to provide variable resistance force to bending along the haptic. For example, a lowered cross-section area or lowered elastic modulus material may be placed one-third the distance from the proximate end of the haptic (where it is joined to optic 23) and one-third the distance from the distal end of the haptic. The spacing of such more deformable segments along a haptic may be selected to allow the haptic to conform more closely to posterior capsule 20, capsule fornix 22 and the inner aspect of the anterior capsule (FIG. 1). Experiments with haptics having different initial shapes and placing variations of resistance to bending of haptics in different locations and observing configurations of the lens-haptic assembly in simulated lens capsules, plus what is well known to those of ordinary skill in the art, may be used to select optimum properties and configurations of haptics.

Figure 2D:
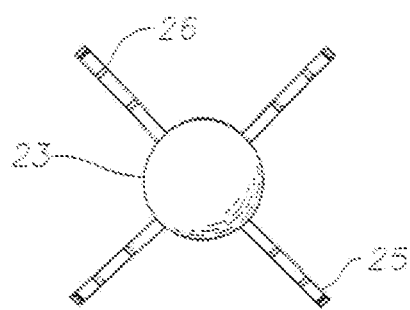

FIG. 2d shows another embodiment of haptics 25. Haptics in this embodiment are strips of biocompatible elastomeric material. Such strips may include areas of weakness 26 placed at selected locations along each haptic, where resistance to bending force is decreased. The bending force on each haptic is selected to hold open a capsule when disposed within, and, preferably, to allow the haptic to conform more closely to posterior capsule 20 and capsule equator or fornix 22 plus the inner aspect of the anterior capsule 19 (FIG. 1). Again, experiments using variations of initial shape and placing resistance to bending of haptics in different locations and observing configurations of the lens-haptic assembly in simulated lens capsules, plus what is known to those of ordinary skill in the art, may be used to select optimum properties and configurations of haptics.

Figure 2E:
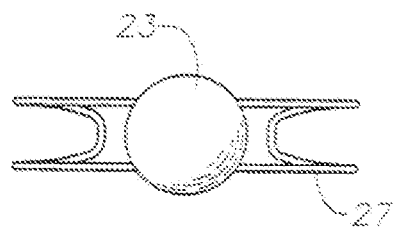
Figure 2G:
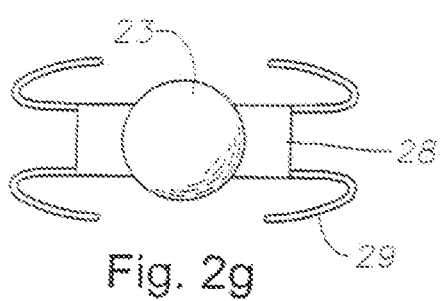
Figure 2F:

FIGS. 2e and 2f illustrate another embodiment of haptics 27. Plan view 2e illustrates haptics forming an elongated loop from lens 23. FIG. 2f illustrates that the haptics may be formed in a shape conforming to the inside of a capsule when no bending force is applied. Haptics 27 preferably fold to near lens 23 for insertion into an eye.

Figure 2H:

FIGS. 2g and 2h illustrate yet another embodiment of haptics 28 and 29. Haptic 28 may be in the form of a plate. Haptics 29 extend from plate 28 and may be formed to conform to the inside of a capsule while extending past the fornix but not to a normal capsulorhexis.

Figures 3A, 3B:
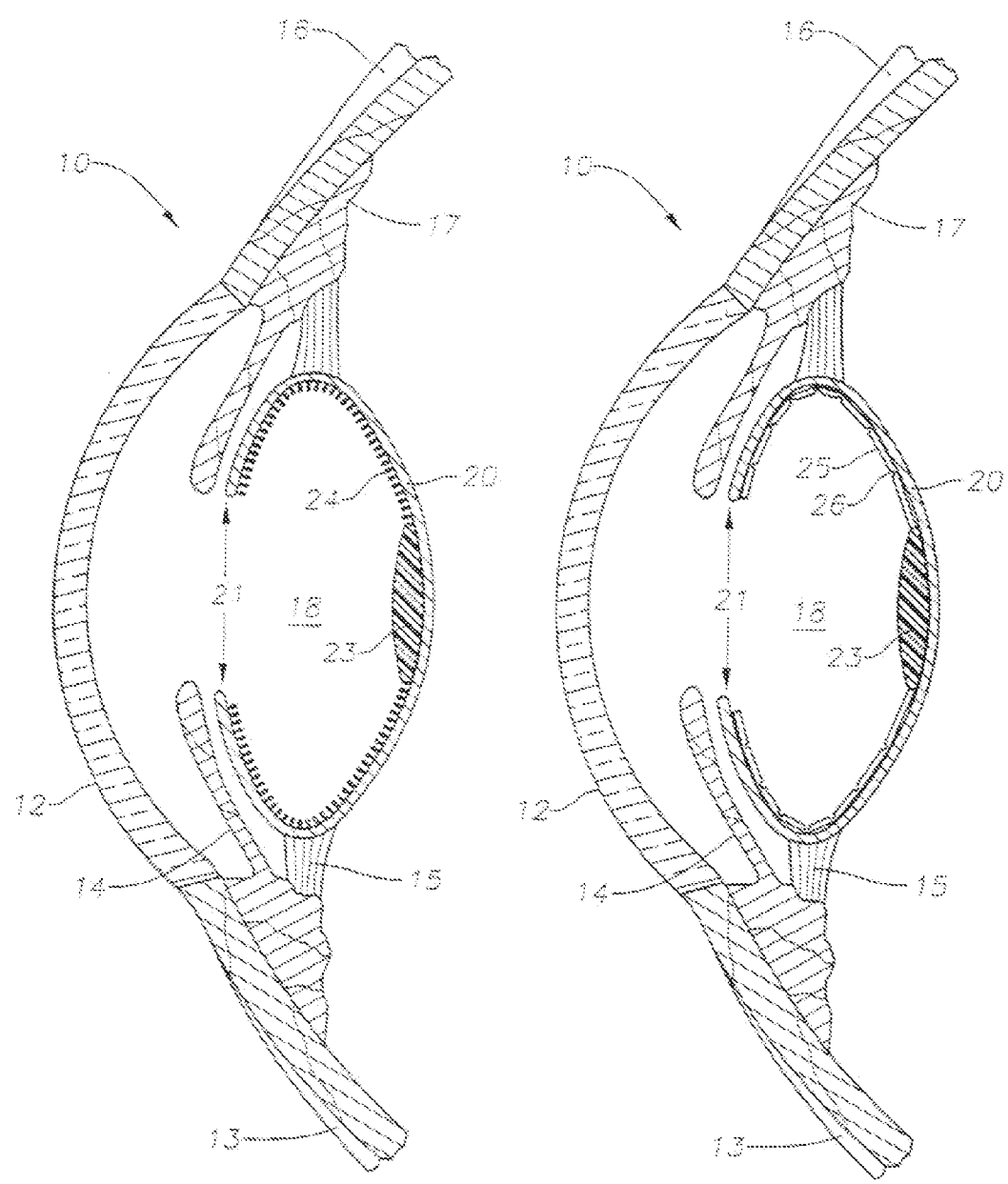
FIG. 3a shows a cross-sectional view of a human eye in which the device of FIG. 2a-b has been placed in the lens capsule.
FIG. 3b shows a cross-sectional view of a human eye in which the device of FIG. 2d has been placed in the lens capsule.
Figure 3C:
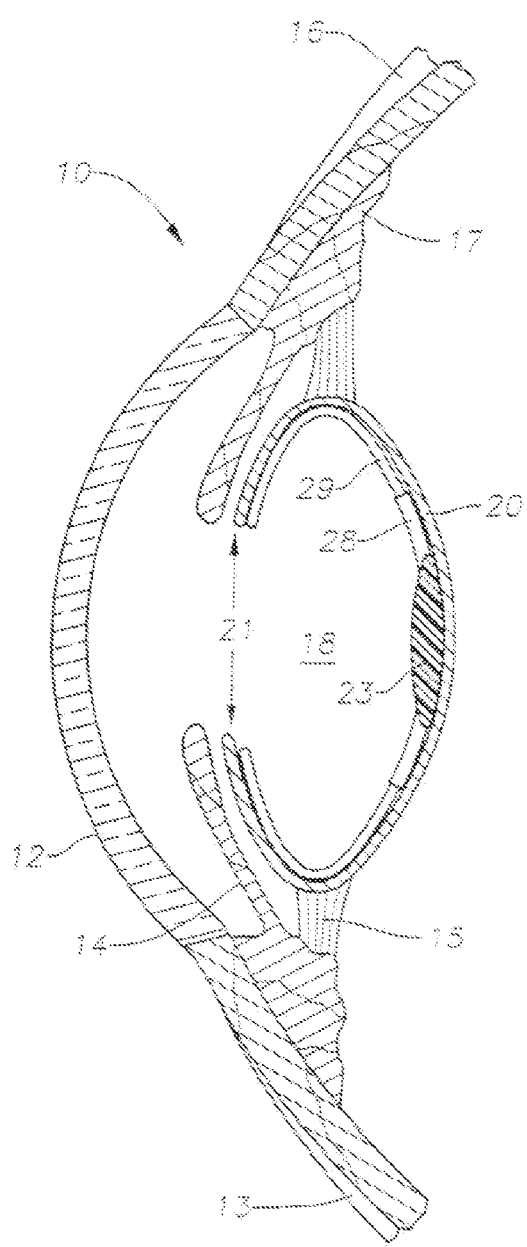
FIG. 3c shows a cross-sectional view of a human eye in which the device of FIG. 2h has been placed in the lens capsule.

FIG. 3a illustrates by cross-sectional view placement of the device of FIGS. 2a-2c in natural lens capsule 18. Lens 23 and haptics 24 are illustrated in FIG. 3a. Forceps or an injector or other device well known to surgeons may be used for placement. Capsulorhexis 21 has been formed in lens capsule 18, or, specifically, in anterior capsule 19 of FIG. 1. Capsulorhexis 21 may also be referred to herein by the term "capsulotomy" or "anterior capsule opening" or "lens capsule opening." In FIG. 3a and other figures disclosed herein, it should be understood that an optic or lens should be designed according to well known methods for each patient, and although only bi-convex lens are shown, the lens may also be planar, concave or suitable combinations thereof. A lens may also be a light-adjustable lens, such as disclosed above. FIG. 3b illustrates by cross-sectional view placement of the device of FIG. 2d in natural lens capsule 18. FIG. 3c illustrates by cross-sectional view placement of the device of FIG. 2g-h in natural lens capsule 18. Preferably, an optic having haptics attached as disclosed herein is placed in lens capsule 18 by the surgeon such that the optic is disposed in contact with posterior capsule 20. Haptics are preferably formed so as to maintain the optic in contact with posterior capsule 20 as it moves in response to ciliary muscle action, which will then produce an accommodating lens system.

Figure 4A:
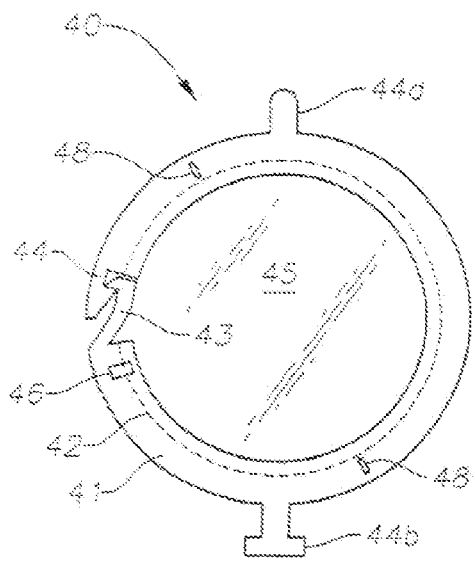
FIGS. 4a and 4b show a plan view and side view of an intracapsulotomy ring to be placed in a capsule opening.

FIG. 4a shows a plan view of device 40 which is adapted for placement in a capsulorhexis such as capsulorhexis 21 of FIG. 3a, in either an anterior or posterior capsule. Ring 42 is a thin, flexible ring adapted to fit inside capsule opening 21, comprising body 42 and groove 41. The ring is normally made from an elastomeric material such as a silane material or other such materials normally used in devices for placement in an eye, and may be referred to herein as an "intracapsulotomy ring.". The ring may be continuous or may be split, as shown in FIG. 4a. Groove 41 is adapted for placement in a lens opening with retention of the anterior 19 or posterior capsule 20 material at the edge of the capsulorhexis within groove 41. The split ring may be placed in the capsule opening with a linear injector similar to the injector used for the Morcher ring, which is well known in the art. After the split ring is placed in the opening, it may be latched to form a continuous structure having an appropriate diameter, using latch 43 and socket 44. Other forms of a latch may be used to join ring body 42 when it is split into a structure having a dimension suitable for the lens opening. One or more eyelets 48 may be placed on ring body 42 or the exterior of groove 41 for suturing device 40 to an iris or other eye tissue. Cleats 44a and 44b may be integral with ring 42 and groove 41. Cleats 44a and 44b may be used to attach a replaceable lens to ring 42 body, as will be further described below In another embodiment, ring body 42 has a hollow core that can be inflated with fluid through sealing valve 46. A cannula (not shown) may be inserted into valve 46 for inflation of ring body 42 to a selected pressure and rigidity after the device is placed in the lens opening. The cannula may then be withdrawn, leaving ring body 42 within the eye. In this embodiment, the ring may not be split, in which case latch 43 and socket 44 are not needed, as ring body 42 is continuous.

Figure 4B:
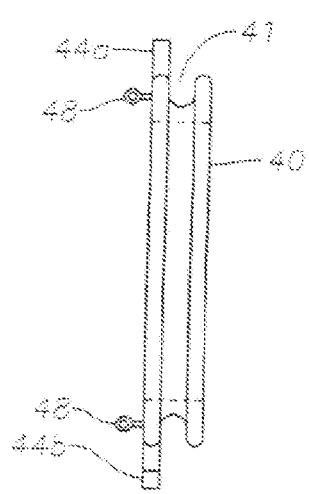

Membrane 45 may be present within ring body 42 of FIG. 4a. Membrane 45 may be integrally formed with ring body 42, may be inserted in ring body 42 separately and latched in place, such as in a groove around the periphery of the ring (not shown). Membrane 45 may be elastic or have elastic segments to provide for operation of a latch when a split ring, such as illustrated in FIG. 4a is used. In another embodiment, membrane 45 may have sufficient rigidity and strength to confine an artificial capsule, as described below, within the natural lens capsule. Membrane 45 may include an optic, such as illustrated by the membrane 56 and 57 of FIG. 5a. FIG. 4b shows a side view of the ring body 42 and groove 41 of FIG. 4a.

Figure 4C:
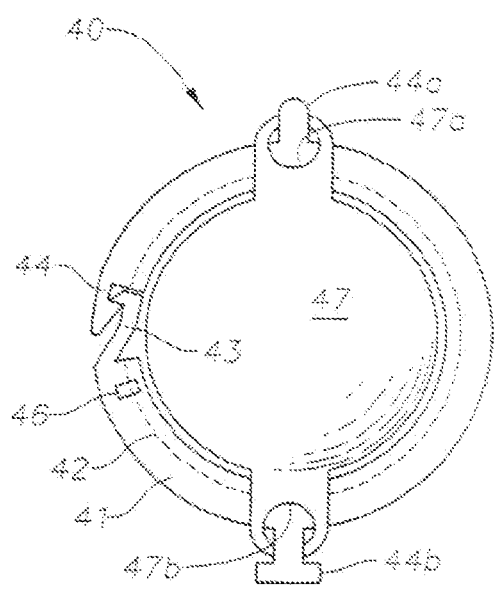
FIG. 4c shows a plan view of the ring of FIG. 4a with an optic attached to the top of the ring.

FIG. 4c illustrates the device 40 of FIG. 4a with lens 47 attached on cleats 44a and 44b. Such detachable lens is described, for example, in U.S. Patent Application No. 2002/0175846, published Nov. 21, 2002, which is hereby incorporated by reference herein. Lens 47 includes openings 47a and 47b, which the surgeon may place over cleats 44a and 44b to hold the lens in place. Lens 47, which may be folded and implanted by normal means, may then be explanted if such procedure is needed for any reason.

Figure 4E:
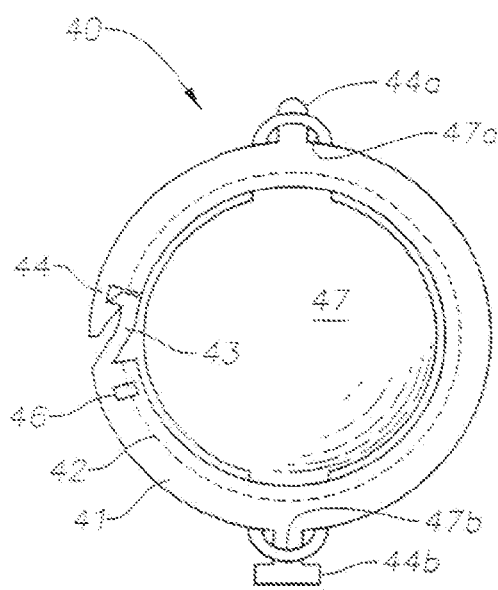
FIG. 4e shows a plan view of the ring of FIG. 4a with an optic attached to the bottom of the ring.
Figure 4D:
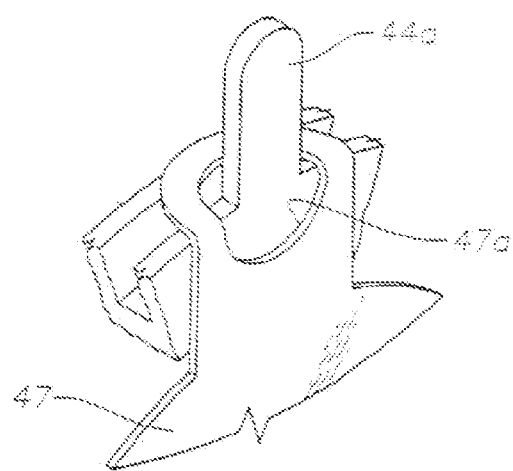
FIG. 4d is an isometric view of a coupling on the optic attached to a pin on the ring.

FIG. 4d is a detailed isometric view of the placement of one embodiment of opening 47a of lens 47 on cleat 44a outside a lens capsule. Elastic properties of ring 42 allow the surgeon to place openings 47a and 47b on the cleats. Ring 42 then provides a radial force outward to maintain the lens in place on the cleats and outside the capsule.

FIG. 4e is a detailed isometric view of the placement of openings 47a and 47b of lens 47 on cleats 44a and 44b inside a lens capsule. Elastic properties of ring 42 allow the surgeon to place openings 47a and 47b on the cleats when the cleats are disposed inside a lens capsule, using the ability of lens 47 to fold. Ring 42 then provides a radial force outward to maintain the lens in place on the cleats inside the capsule.

An alternate embodiment of an intracapulotomy ring for a capsule opening is shown in FIGS. 5a and 5b. FIG. 5a shows a plan view of ring 51 having tabs 52 disposed around the ring, the tabs being spaced apart a distance selected to receive and retain the periphery of a capsulorhexis in the anterior or posterior capsule of an eye within the tabs. Ring 51 may be latched into an approximately circular configuration by latch pin 54 and latch receptor 55. Other forms of latch mechanisms may be used to bring ring 51 together. The ring may also be inserted by a tool similar to that used to insert a Morcher ring. Within ring 51 membrane 56 may be present, and lens 57 may be included in membrane 56. Such parts may be formed integrally with ring 51 or may be separately installed in ring 51 before or after ring 51 is placed in an eye, as disclosed in regards to FIG. 4. Eyelets 58 may be present at selected positions to provide for suturing to eye tissue. Cleats 51a and 52b may be present to provide a mechanism to attach a replaceable lens to device 50, as more particularly described below. FIG. 5b shows a side view cross-section of the device also shown in FIG. 5a.

FIG. 5c illustrates the device 50 of FIG. 5a (without membrane 56 and lens 57) but with lens 59 attached on cleats 51a and 51b. Such detachable lens is described, for example, in U.S. Patent Application No. 2002/0175846, published Nov. 21, 2002, discussed above. Lens 59 includes openings 59a and 59b, which the surgeon may place over cleats 51a and 51b to hold the lens in place. Lens 59, which may be folded and implanted by otherwise normal means, may then be explanted if such procedure is needed.

Figure 6:
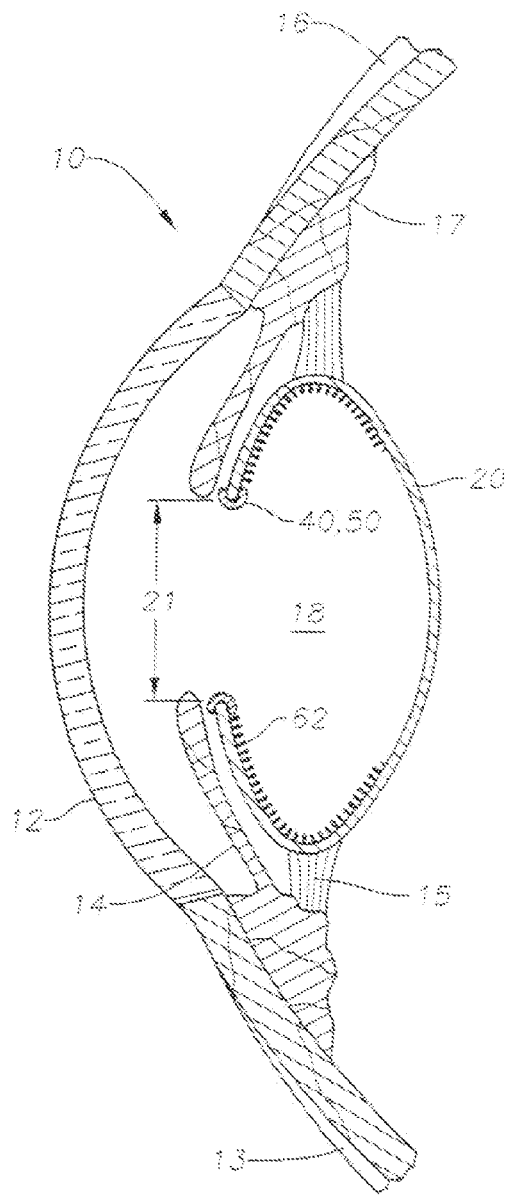
FIG. 6 shows a cross-sectional view of an eye having an intracapsulotomy ring with haptics attached placed in the capsule opening.

FIG. 6 depicts in cross-section in an eye the device 40 of FIG. 4 or the device 50 of FIG. 5, further having attached to the device haptic 62. Haptic 62 may have the form such as shown in FIG. 2, for example. Such ring and haptic combination may be used to hold open capsule 18 after a surgical procedure. Device 40 or 50 (FIG. 4 or 5) may, alternatively, be placed in an opening in posterior capsule 20 (FIG. 1), not shown. Such device may be employed for preventing fibrosis or growth of a capsule opening toward closure after surgery. Such devices may be particularly useful in pediatric ophthalmic surgery, where closure of capsule openings by tissue growth is more rapid, as well as in treating a condition such as pseudo-exfoliation syndrome.

Figure 7:
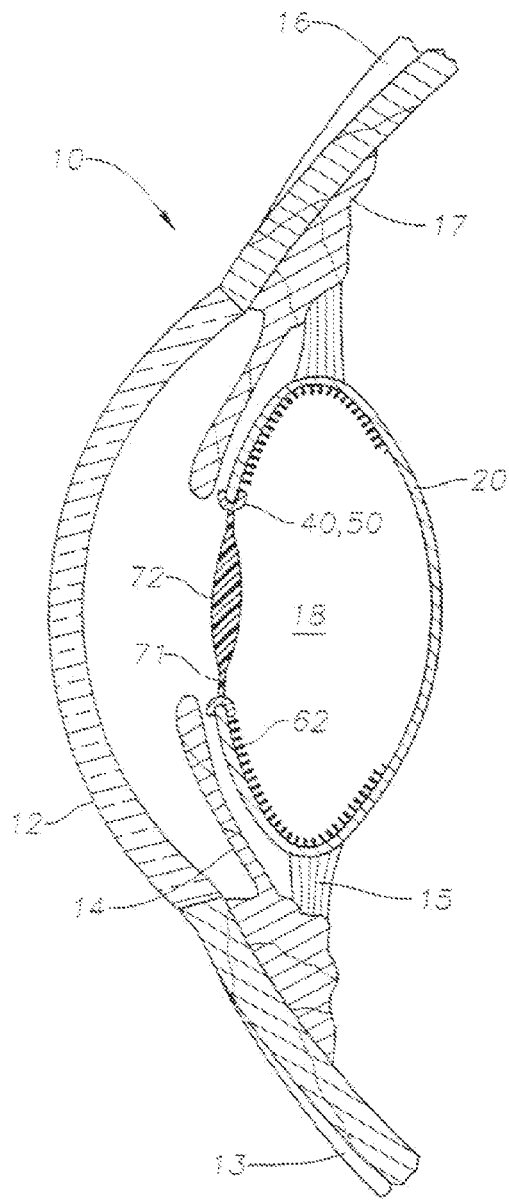
FIG. 7 shows a cross-sectional view of an eye with an intracapsulotomy ring in the capsule opening, the ring having within a membrane and/or optic, with haptics attached to the ring.

FIG. 7 illustrates the device of FIG. 6 after placement of membrane 71 and optic 72 within the ring 40 or 50 of FIGS. 4 and 5. Haptic 62 of FIG. 6 is also shown. Haptic 62 may not be used in some cases. Alternatively, a haptic such as shown in FIGS. 2c through 2h or other forms of haptics may be employed. Membrane 71 may be used without optic 72. Also, optic 72 may extend throughout a ring without the presence of membrane 71. The device including ring 40 or 50, membrane 71, optic 72, and haptic 62 may be formed integrally or may be formed by joining of separate component parts. Materials may be materials known in the art to be useful in optical devices for implantation in a human or animal eye. In another embodiment, a lens such as illustrated in FIG. 4c-e or FIG. 5c may be employed with the lens and haptics of FIG. 2a-h. The length of haptics may be adjusted to accommodate both anterior and posterior lens.

Figure 8:
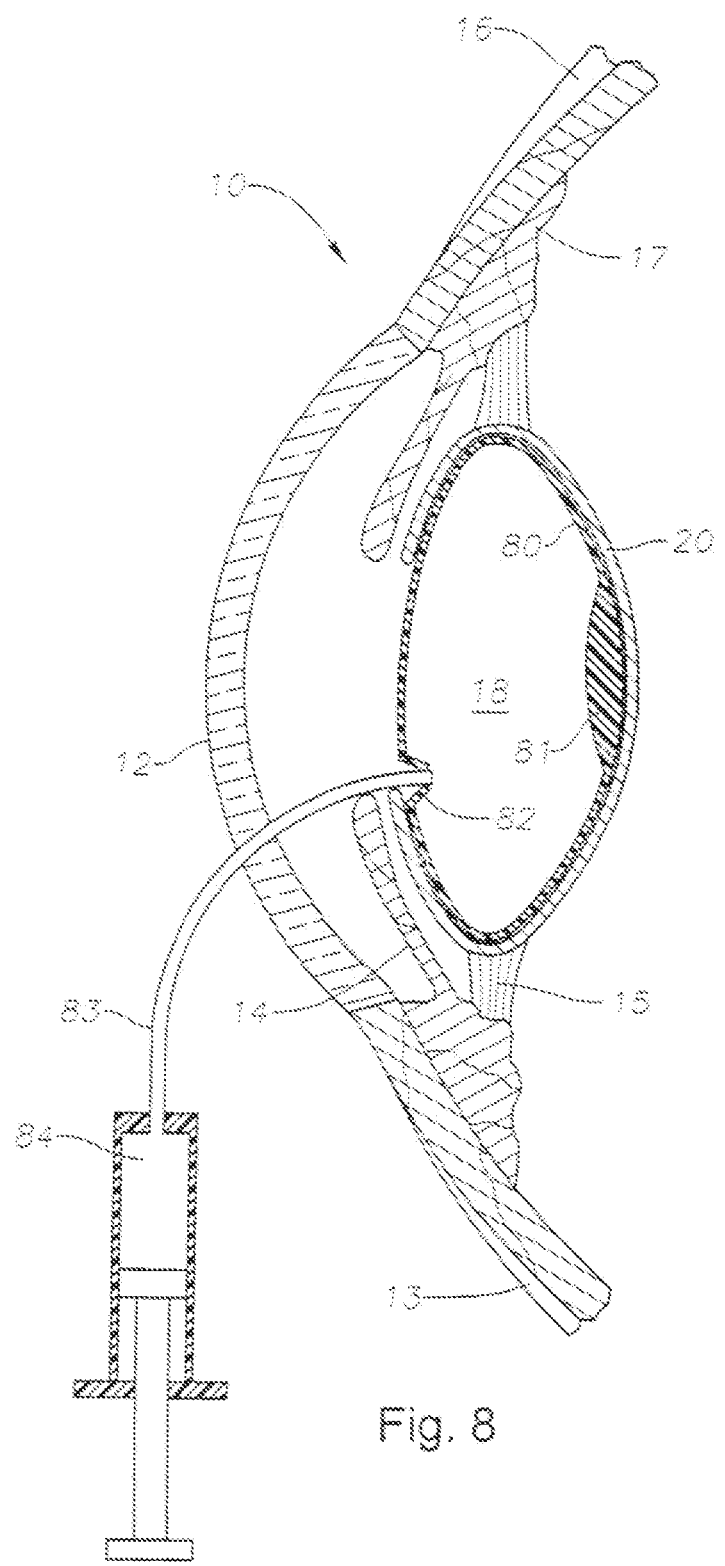
FIG. 8 shows a cross-sectional view of an eye having an artificial capsule placed within the lens capsule, the artificial capsule being attached to apparatus for inflating the capsule and having an optic within.

Referring to FIG. 8, another embodiment of the device to hold apart anterior and posterior capsules and maintain the natural capsule shape is shown at 80. Artificial capsule 80 may be constructed of plastic material suitable for biomedical use, such as a silane material. The wall thickness or elastic constants of the material of the wall of capsule 80 may vary to cause artificial capsule 80 to conform more closely to the shape of a natural lens capsule. Optimum variations may be determined by experiment in a simulated lens capsule. as explained above relative to the use of haptics. Optic 81 may be formed within artificial capsule 80. Valve 82 may be present in capsule 80 to allow the capsule to be inflated with a selected liquid or gel after placement through capsulorhexis 21 (FIG. 3). Cannula 83 may be inserted in valve 82 and pump or syringe 84 may be used for injection of a selected fluid into artificial capsule 80. The fluid used may be selected for refractive index and biomedical properties. Artificial capsule 80 may be folded and placed in the natural capsule through capsulorhexis 21 (such as shown in FIG. 3) and then inflated to a desired volume. The location of optic 81, if present, may be adjusted prior to inflation and during inflation of artificial capsule 80. Valve 82 preferably seals after removal of cannula 83.

Figure 10:
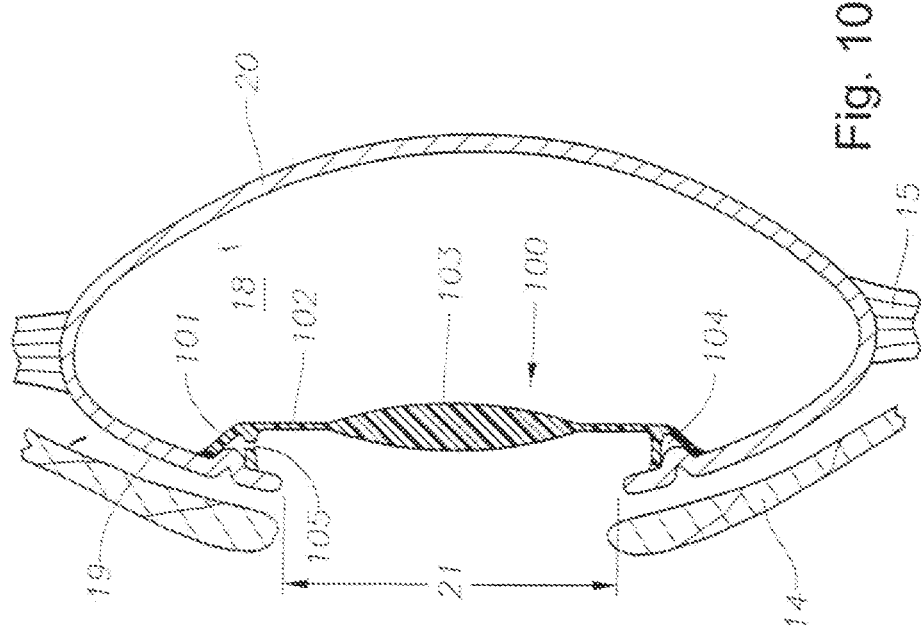
FIG. 10 shows a cross-sectional view of a ring and membrane forming an artificial anterior capsule, the ring being attached to the natural lens capsule by a pinching mechanism, the membrane including an optic and membrane.
Figure 9:
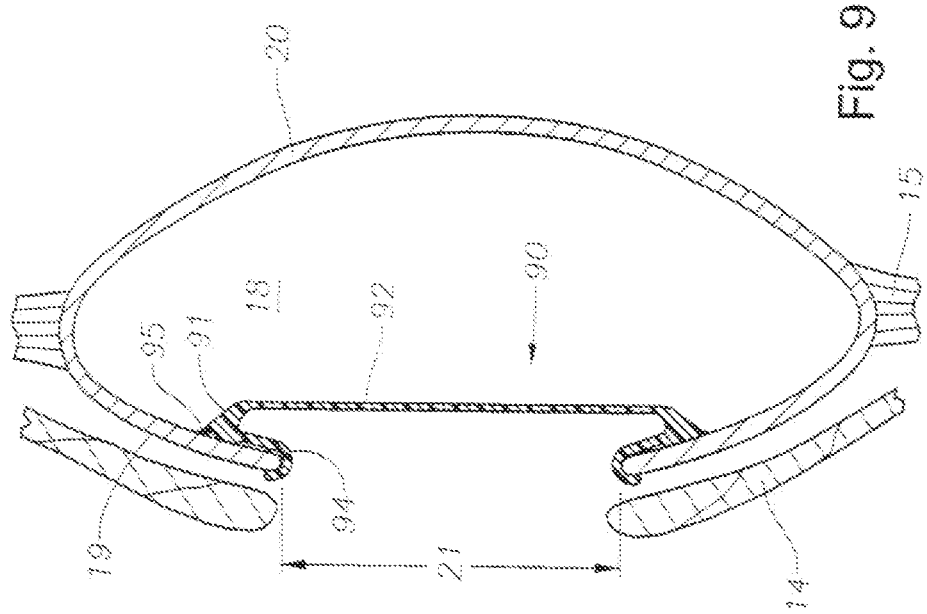
FIG. 9 shows a ring and membrane apparatus attached to a natural anterior capsule to form an artificial anterior capsule, the ring being attached by a collar.

Referring to FIG. 9, apparatus 90 for forming an artificial anterior capsule is illustrated by a cross-sectional view. Ring 91 includes membrane 92. Membrane 92 may be deformable to accommodate movement of any contents of capsule 18 in response to ciliary muscle action. Ring 91 has attached thereto collar 94, which is adapted for receiving natural anterior capsule 19 at the periphery of capsulotomy 21. Similar apparatus is disclosed in U.S. patent application Ser. No. 10/888,298, titled "Apparatus and Methods for Isolating Lens Capsule Fluids," filed Jul. 9, 2004, which is hereby incorporated by reference herein. The referenced patent application discloses use of a device such as disclosed in FIG. 9 (and FIG. 10) during surgery, except that the device includes a port for injecting or aspirating fluids to or from capsule 18. This procedure may be used to "polish" the capsule to remove cells that may later cause fibrosis or PCO. Such procedure is preferably used before implantation of the devices disclosed herein. Device 90 may be implanted in an eye for various reasons after surgery. Membrane 92 may include an optic, as illustrated in FIG. 10. Apparatus 90 will normally be made of an elastomeric biomedically approved material, such as a silane material, or combinations of such materials. Ring 91 may include colorant 95. Such colorant may be used by a surgeon in locating ring 91 with respect to a capsulorhexis during a surgical procedure. Tissue adhesive may be placed within collar 94 for forming a bond with anterior capsule 19. Such tissue adhesives are well known in the art. The dimensions of capsulorhexis 21, as illustrated in FIG. 3, determines the preferred dimensions of ring 91 and membrane 92. Preferably, different sizes of ring 91 and membrane 92 are available to the surgeon for application in different cases. Oval or other non-rounded shapes may be formed and applied in cases when a capsulorhexis is not round. Although membrane 92 is shown inside capsular lens 18 in FIG. 9, it should be understood that collar 94 may be placed so that membrane 92 is disposed outside capsular lens 18.

Referring to FIG. 10, an alternative embodiment for placing a membrane and ring within the lens capsule to form an artificial anterior capsule is illustrated by a cross-sectional view. Ring 101 includes flow channel 104. Contacting flow channel 104 is port 105. A cannula (not shown) may be inserted into port 105 and reduced pressure applied within channel 104. Ring 101 is adapted to contact the posterior surface of anterior capsule 19 before the reduced pressure is applied in channel 104. When the reduced pressure is applied, anterior capsule 19 is pulled into channel 104. The structure of ring 101 is designed to pinch and permanently hold anterior capsule 19 within channel 104. Similar apparatus and method are disclosed in U.S. application Ser. No. 10/888,298, filed Jul. 9, 2004, which is incorporated by reference herein. The procedure that may be used to cause anterior capsule 19 to be attached to ring 101 is disclosed in Paragraph 25 of the subject application. A segment of anterior capsule 19 in the form of a ring is shown folded to enter a portion of flow channel 104 within ring 101. Ring 101 is constructed to receive the segment of anterior capsule 19 in contact with ring 101 when a sufficiently reduced pressure is applied to the sealing area between ring 101 and the posterior surface of anterior capsule 19. The reduced pressure in flow channel 104 pulls anterior capsule 19 into flow channel 104. Further, ring 101 is constructed to pinch anterior capsule 19 with sufficient force to keep the segment of anterior capsule in place within ring 101 and form a permanent seal of device 100 to anterior capsule 19, thus sealing and isolating volume 18 of the capsule. This pinching arrangement may be supplied by elasticity properties in ring 101 or by other mechanical spring force applied radially in ring 101. A ridge running along within flow channel 104 may be used to decrease the width of flow channel 104 before it is intersected by port 105, so as to keep flow channel 104 open throughout ring 101. Alternatively, a perforated partition may be placed in flow channel 104 so as to limit movement of a ring of anterior capsule 19 into flow channel 104.

Membrane 102, included within ring 101, may include optic 103. Membrane 102 may be deformable to accommodate movement of any contents of capsule 18 in response to ciliary muscle action. The dimensions of capsulorhexis 21, as illustrated in FIG. 3, determines the preferred dimensions of ring 101 and membrane 102. Preferably, different sizes of ring 101 and membrane 102 are available to the surgeon for application in different cases. Oval or other non-rounded shapes may be formed and applied for cases when the capsulorhexis is not round. Although membrane 102 is shown inside capsular lens 18, it should be understood that collar 104 may be placed so that membrane 92 is disposed outside capsular lens 18.

Figure 11:
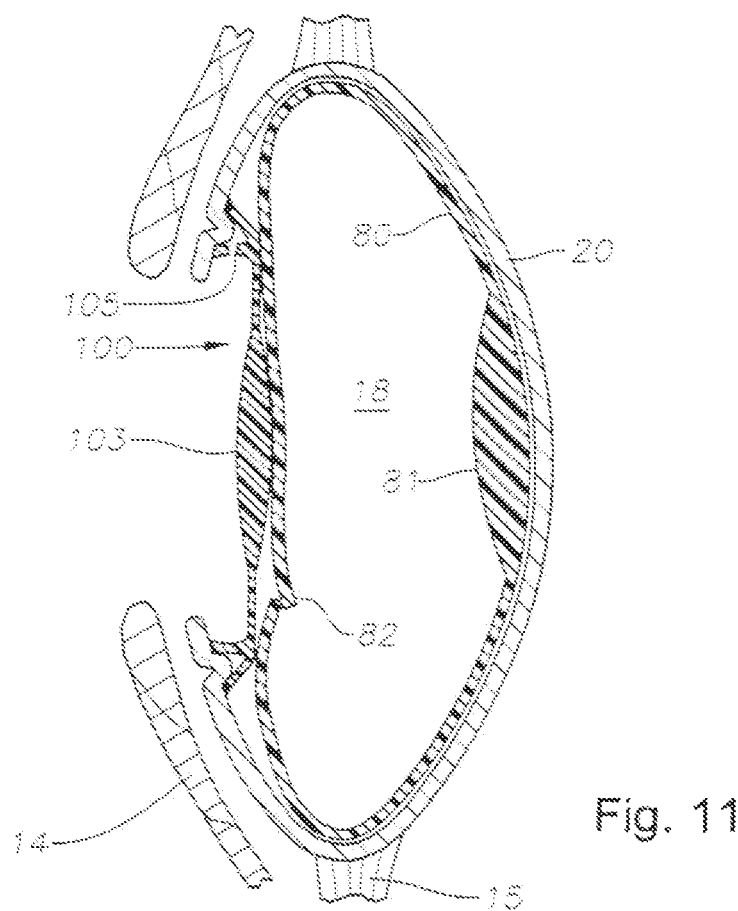
FIG. 11 shows a cross-sectional view of the human eye in which an artificial capsule has been implanted, the capsule including an optic, and an artificial anterior capsule has also been implanted, the artificial anterior capsule including a ring attached by a pinch seal to the anterior capsule and including a second optic.

FIG. 11 illustrates in a cross-sectional view one combination of apparatus described in previous drawings. Artificial capsule 80 of FIG. 8 is shown implanted within natural capsule 18, where it has been implanted through a capsule opening. It has normally been inflated through valve 82, and may contain optic 81. After artificial capsule 80 is in place and inflated, device 100, illustrated in FIG. 10, may be implanted. Device 100 may contain lens 103, as shown in FIG. 10. In this application, two optics, 81 and 103, are placed in the eye. Dual optics are known in the art for forming an accommodating lens. Techniques for designing the configuration of each lens are well known in the art, using dimensions separating the lenses. Movement of optic 81 in an anterior or posterior direction, caused by ciliary muscle 17 (FIG. 1), would provide accommodation for such compound lens apparatus. Other combinations of the devices disclosed herein may be used to obtain dual optic systems, adjusting haptics to allow placement of the devices in the capsular lens.

Although the disclosures herein have been primarily described with respect to application in human eyes, it should be understood that the apparatus and methods may be used in all animals and reference to "eye" or "human eye" herein includes an eye of any animal.

Although the present invention has been described with reference to specific details, it is not intended that such details should be regarded as limitations on the scope of the invention, except as and to the extent they are included in the accompanying claims.

What I claim is:

1. A device to be placed in an anterior capsule opening of an eye, the anterior capsule opening having a periphery, comprising:
   a ring and a membrane therewithin, the ring being adapted to form a sealing area between the ring and a surface of the anterior capsule, the sealing area configured for fluid communication with a conduit extending outside the capsule; and
   the ring having a flow channel, said flow channel having a port connected and a port thereto whereby when the ring contacts the posterior surface of the anterior capsule of the eye, reduced pressure may be applied in the flow channel which pulls a portion of the anterior capsule into the flow channel thereby securing the membrane.

2. A dual optic lens system for an eye comprising:
   a first optic adapted to be located within the lens capsule adjacent a posterior portion thereof,
   a second optic adapted to be positioned within an opening in an anterior portion of the lens capsule,
   means for securing the second optic within the opening, and
   the means for securing the second optic within the opening comprises a ring attached to the optic and having a flow channel, said flow channel having a port connected thereto, whereby when the ring contacts a posterior surface of the anterior capsule of the eye, reduced pressure may be applied in the flow channel which pulls a portion of the anterior capsule into the flow channel thereby securing the optic.

3. A device to be placed in an anterior capsule opening of an eye, the anterior capsule opening having a periphery, comprising:
   a ring and a membrane therewithin, the ring being adapted to form a sealing area between the ring and a surface of the anterior capsule, the sealing area configured for fluid communication with a conduit extending outside the capsule;
   said membrane including an optic within the ring; and
   the ring having a flow channel, said flow channel having a port connected thereto, whereby when the ring contacts a posterior surface of the anterior capsule of the eye, reduced pressure may be applied in the flow channel which pulls a portion of the anterior capsule into the flow channel thereby securing the membrane.

* * * * *